United States Patent [19]

Imai et al.

[11] 4,267,387
[45] May 12, 1981

[54] PROCESS FOR PREPARATION OF AROMATIC HYDROPEROXIDES

[75] Inventors: Ichiro Imai, Ohtake; Isao Hashimoto, Iwakuni; Keiji Suzuki, Ohtake; Hiroaki Nakagawa, Iwakuni, all of Japan

[73] Assignee: Mitsui Petrochemical Industries Ltd., Tokyo, Japan

[21] Appl. No.: 85,587

[22] Filed: Oct. 17, 1979

[51] Int. Cl.³ .................................. C07C 179/035
[52] U.S. Cl. .................................................... 568/568
[58] Field of Search .......................................... 568/568

[56] References Cited

U.S. PATENT DOCUMENTS 2,735,871  2/1956  Smith .................................. 568/568

FOREIGN PATENT DOCUMENTS

| | | |
|---|---|---|
| 680834 | 2/1964 | Canada .................................. 568/568 |
| 2737202 | 2/1978 | Fed. Rep. of Germany . |
| 35-13824 | 9/1960 | Japan . |
| 910735 | 11/1962 | United Kingdom . |
| 1024811 | 4/1966 | United Kingdom .................. 568/568 |

*Primary Examiner*—Werren B. Lone
*Attorney, Agent, or Firm*—Sherman & Shalloway

[57] ABSTRACT

An improved process for the preparation of an aromatic hydroperoxide by oxidizing a hydroxyalkyl-substituted aromatic compound having at least one hydroxyalkyl group directly bonded to an aromatic ring carbon of the aromatic compound and being represented by the formula

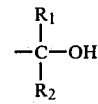

wherein $R_1$ and $R_2$ each are a lower alkyl group, with hydrogen peroxide in the presence of an acid catalyst in a heterogeneous system of a water-immiscible inert aromatic hydrocarbon solvent at a reaction temperature of up to about 70° C. while removing by-product water as an azeotrope with the aromatic hydrocarbon solvent in the oxidation system; characterized in that said oxidation is carried out while feeding a vapor of a water-immiscible inert aromatic hydrocarbon solvent having a temperature higher than the reaction temperature but not exceeding about 90° C. into a liquid phase of the oxidation system.

12 Claims, No Drawings

PROCESS FOR PREPARATION OF AROMATIC HYDROPEROXIDES

This invention relates to an improved process for preparing aromatic hydroperoxides by oxidizing hydroxyalkyl-substituted aromatic compounds with hydrogen peroxide in the presence of acid catalysts. Particularly, the present invention provides an improved process by which the aforesaid oxidation can be carried out commercially advantageously with an excellent heat efficiency and a uniform heating effect to achieve an improved yield of the aromatic hydroperoxide, an improved ratio of cleavage and a reduced percent loss of hydrogen peroxide.

More specifically, the invention pertains to a process for the preparation of an aromatic hydroperoxide by oxidizing a hydroxyalkyl-substituted aromatic compound having at least one hydroxyalkyl group directly bonded to an aromatic ring carbon of the aromatic compound and being represented by the formula

wherein $R_1$ and $R_2$ each represent a lower alkyl group, with hydrogen peroxide in the presence of an acid catalyst in a heterogeneous system of a water-immiscible inert aromatic hydrocarbon solvent at a reaction temperature of up to about 70° C. while removing by-product water as an azeotrope with the aromatic hydrocarbon solvent in the oxidation system; characterized in that said oxidation is carried out while feeding a vapor of a water-immiscible inert aromatic hydrocarbon solvent having a temperature higher than the reaction temperature but not exceeding about 90° C. into a liquid phase of the oxidation system.

The production of an aromatic hydroperoxide by the oxidation of an alkyl-substituted aromatic compound with molecular oxygen such as air has been well known, and this reaction is an important step which constitutes part of the commercial process for production of phenols and carbonyl compounds. In this oxidation reaction, the formation of hydroxyalkyl-substituted aromatic compounds as a by-product cannot be avoided, and makes it impossible to increase the yield of the final desired product. It was suggested to oxidize the oxidation reaction mixture including such by-product carbinols with hydrogen peroxide in the presence of an acid catalyst, thereby converting the by-product hydroxyalkyl-substituted aromatic compound into the corresponding aromatic hydroperoxide, and to cleave the aromatic hydroperoxide with an acid to form phenols and carbonyl compounds.

For example, British Pat. No. 910,735 (published on Nov. 21, 1962) discloses that in the production of hydroquinone by acid-cleavage of an oxidation product of p-diisopropylbenzene, the by-product p-substituted carbinol does not change to hydroquinone, but by treating this by-product with an acid catalyst in the presence of hydrogen peroxide in an homogeneous system of an inert solvent solution in a single step, it can be converted to hydroquinone.

It was also suggested in Japanese Patent Publication No. 13824/60 (published on Sept. 21, 1960) to prepare phenols by treating by-product carbinols present in the oxidation products of alkylbenzenes with hydrogen peroxide in one step in the presence of an acid catalyst in a heterogeneous system.

U.S. Pat. No. 2,735,871 discloses a method of treating an impure aralkyl hydroperoxide containing oxygen-containing organic impurities in order to increase the purity thereof which comprises contacting said aralkyl hydroperoxide with hydrogen peroxide in the presence of an acid at a temperature in the range of from about −60° C. to about 35° C., maintaining said hydroperoxide at a temperature below about 35° C. at all times while in contact with said acid, and correlating the time of contact of said acid with said hydroperoxide and the temperature at which the resulting mixture is maintained to effect said treatment in the absence of any substantial cumene hydroperoxide decomposition. This method, however, has the disadvanatage that in a system in which the desired phenol is prone to react with the by-product hydroxyalkyl-substituted aromatic compound as in the production of resorcinol from m-diisopropylbenzene, the two react with each other and the desired phenol is consumed so that its yield is decreased.

In an attempt to overcome this disadvantage, there was suggested an improved process for producing dihydroxybenzenes, especially resorcinol, by the acid cleavage of oxidation products of diisopropylbenzenes, especially m-diisopropylbenzene, with hydrogen peroxide and an acid catalyst such as sulfuric acid, which comprises a first step of pretreating the starting oxidation product of diisopropylbenzene in the presence of hydrogen peroxide in a heterogeneous system in an aqueous aromatic hydrocarbon solvent under conditions which do not substantially cause acid cleavage, while removing the by-product water as an azeotrope with the aromatic hydrocarbon in the treating system, and a second step of cleaving the pretreated product with an acid catalyst in the substantial absence of hydrogen peroxide (Japanese Laid-Open Patent Publication No. 23939/78; West German Laid-Open Patent Application, OLS, No. 2737302).

In the oxidation reaction of the hydroxyalkyl-substituted aromatic compound with hydrogen peroxide, the generation of the heat of reaction is relatively small. It is necessary therefore to supply heat to the reaction system so as to secure an amount of heat required to remove the by-product water as an azeotrope. However, it was found in the prior art that in commercial scale operations, it is difficult to supply heat with a uniform heating effect and a good heat efficiency without involving the undesirable decomposition of the resulting aromatic hydroperoxide.

It has also been found that in addition to the reduced yield of the phenol formed by the decomposition of the aromatic hydroperoxide which is due to its reaction with the by-product hydroxyalkyl-substituted aromatic compound, the aforesaid prior technique has the disadvantage that in the reaction system subject to heating conditions, the heat of reaction is generated incident to the decomposition of the aromatic hydroperoxide, and is likely to cause an abrupt increase in the temperature of the reaction system, and moreover, in order to avoid build-up of the phenol in the aqueous phase of the reaction system, a measure should be taken to remove it.

The present inventors have made extensive investigations in order to overcome the aforesaid disadvantages which arise anew in the commercial-scale performance of the oxidation of the hydroxyalkyl-substituted aromatic compound with hydrogen peroxide in the presence of an acid catalyst. The investigations have led to the discovery that these disadvantages can all be overcome by a simple means of performing the above oxidation while feeding a vapor of a water-immiscible inert aromatic hydrocarbon solvent at a specified temperature into a liquid phase of the oxidation system.

It has also been found that the improvement contemplated by the present invention cannot be achieved then an inert gaseous material such as nitrogen gas is used instead of the vapor of a water-immiscible inert aromatic hydrocarbon solvent. Furthermore, it has been found that both the latent heat and sensible heat of the vapor of a water-immiscible inert aromatic hydrocarbon solvent can be utilized, and the amount of the vapor can be about 1/15 to 1/20 of that of the inert gaseous material thus showing a far better heat efficiency and that localized overheating can be advantageously avoided.

It is an object of this invention therefore to provide an improved process for the preparation of an aromatic hydroperoxide by oxidizing a hydroxyalkyl-substituted aromatic compound with hydrogen peroxide in the presence of an acid catalyst while removing by-product water as an azeotrope.

The above and other objects and advantages of this invention will become more apparent from the following description.

According to the process of this invention, a hydroxyalkyl-substituted aromatic compound having at least one hydroxyalkyl group directly bonded to an aromatic ring carbon of the aromatic compound and being represented by the formula $$\begin{array}{c} R_1 \\ | \\ -C-OH \\ | \\ R_2 \end{array}$$

wherein each of $R_1$ and $R_2$ represents a lower alkyl group,
is oxidized with hydrogen peroxide in the presence of an acid catalyst. The oxidation is carried out at a temperature of up to about 70° C. in a heterogeneous system of a water-immiscible inert aromatic hydrocarbon solvent while removing the by-product water as an azeotrope with the aromatic hydrocarbon solvent in the oxidation system.

According to the process of this invention, the oxidation is carried out while feeding a vapor of a water-immiscible inert aromatic hydrocarbon solvent having a temperature higher than the reaction temperature but not exceeding about 90° C. into a liquid phase of the oxidation system.

The hydroxyalkyl-substituted aromatic compound may have another substituent such as an alkyl or hydroperoxyalkyl group in addition to the hydroxyalkyl group of the formula $$\begin{array}{c} R_1 \\ | \\ -C-OH. \\ | \\ R_2 \end{array}$$

In the above formula, $R_1$ and $R_2$ are preferably both lower alkyl groups, especially methyl groups. Specific examples of the hydroxyalkyl-substituted aromatic compound include the following.

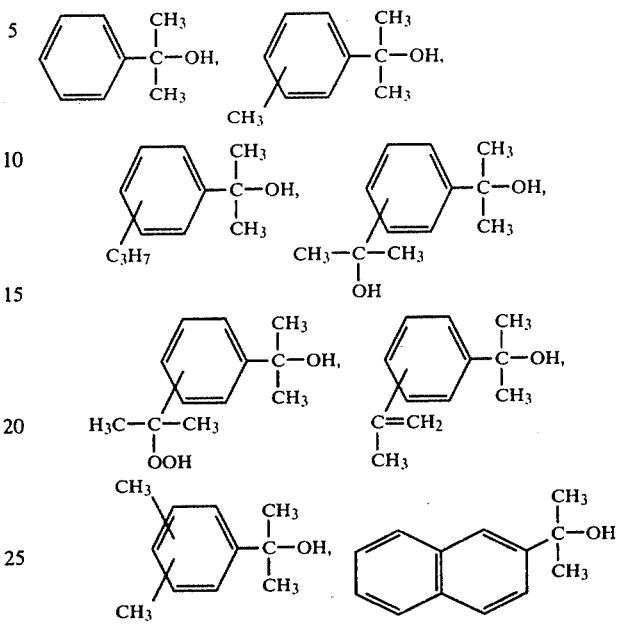

These hydroxyalkyl-substituted aromatic compounds can be obtained as by-products in the production of aromatic hydroperoxides by the liquid-phase auto-oxidation of alkyl-substituted aromatic compounds, preferably isopropyl aromatic compounds such as cumene, m-cymene, p-cymene, dimethylcumene, m-diisopropylbenzene, p-diisopropylbenzene isopropylnaphthalene, or mixtures of these. The process of this invention exhibits a greater effect when applied to oxidation reaction products containing such aromatic hydroperoxides and hydroxyalkyl-substituted aromatic compounds.

The process of this invention can be advantageously applied to the production of an aromatic hydroperoxide by the oxidation of a hydroxyalkyl-substituted aromatic compound, particularly an oxidation product of m-diisopropylbenzene composed of m-diisopropylbenzene dihydroperoxide and by-product m-substituted carbinol hydroperoxide and/or dicarbinol. In other words, the most suitable hydroxyalkyl-substituted aromatic compounds are

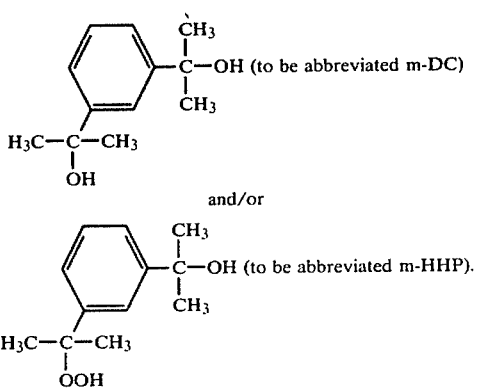

Above all, an oxidation product of m-diisopropylbenzene containing these compounds and m-diisopropylbenzene dihydroperoxide (to be referred to as m-DHP)

is preferred. When the oxidation product of an alkyl aromatic compound is used as the starting material, the unreacted alkyl aromatic compound or other unwanted materials may be removed from it prior to the reaction.

The reaction in accordance with this invention is carried out in the presence of an inert aromatic hydrocarbon solvent which dissolves the hydroxyalkyl-substituted aromatic compounds or the oxidation reaction products of alkylaromatic compounds, is immiscible with water, and azeotropes with water. Examples of suitable inert aromatic hydrocarbon solvents include benzene, toluene, xylene, ethylbenzene, cumene, trimethylbenzene, cymene, diethylbenzene, butylbenzene, and diisopropylbenzene. Aromatic hydrocarbons having a relatively low boiling points, such as benzene, toluene, xylene and ethylbenzene, are preferred. These solvents may be used singly or in combination with each other. An aliphatic hydrocarbon or alicyclic hydrocarbon, if in a small amount, may be present in the inert aromatic hydrocarbon solvent.

The amount of the water-immiscible inert aromatic hydrocarbon solvent used may be selected as desired. For example, it is about 0.2 to about 10 times, preferably about 0.5 to about 2 times, the weight of the hydroxyalkyl-substituted aromatic compound or the oxidation product of the alkyl-substituted aromatic compound.

Preferably, the hydrogen peroxide is used in the form of an aqueous solution having a concentration of about 10 to about 40% by weight. The amount of hydrogen peroxide can be selected as desired, and is, for example, about 0.5 to about 20 equivalents, preferably about 2 to about 15 equivalents, per mole of the hydroxyl groups of the hydroxyalkyl-substituted aromatic compound. Hydrogen peroxide which is used in an excessive amount and remains unreacted may be separated from the reaction mixture for re-use.

The acid catalyst used in the reaction is preferably water-soluble. Examples include inorganic acids such as sulfuric acid, perchloric acid, hydrochloric acid and phosphoric acid, and organic acids such as formic acid, chloroacetic acid, and p-toluenesulfonic acid. Sulfuric acid is most preferred. The amount of the acid catalyst can be properly selected depending upon the type of the acid, the amount of water in the reaction system, the reaction temperature, etc. The suitable amount of the acid catalyst is that which does not induce acid cleavage of the aromatic hydroperoxide under the oxidation conditions. The preferred concentration of the acid catalyst in an aqueous solution of hydrogen peroxide in the oxidation system is about 0.5 to about 5 moles/liter.

Water formed as a by-product of the reaction is withdrawn out of the reaction system through the upper portion of the reaction zone as an azeotrope with the aromatic hydrocarbon solvent in the oxidation system, thereby controlling the proportion of water in the reaction system. The reaction temperature that may be used in the process of this invention is up to about 70° C., usually about 20° C. to about 70° C., preferably about 30° C. to about 60° C. To form the azeotrope advantageously, it is convenient to maintain the reaction system under reduced pressure. The pressure is, for example, about 30 to about 300 mm Hg although it may be varied depending upon the type of the hydrocarbon solvent used, the type of the hydrocarbon solvent supplied as a vapor, etc.

In order to supply heat required for the above azeotropic distillation of water, the vapor of a water-immiscible inert solvent is fed into the reaction system, and the heat of condensation of the vapor and at times, possible heat are advantageously utilized. Suitable water-immiscible inert solvents are hydrocarbons which are condensed under the reaction conditions. The above-exemplified aromatic hydrocarbon solvents which can be used as a reaction solvent are preferred.

The temperature of the vapor of the aromatic hydrocarbon solvent is higher than the reaction temperature but does not exceed about 90° C., and the reaction is carried out while the aromatic hydrocarbon solvent vapor is introduced into the liquid phase of the oxidation reaction system. The preferred temperature of the vapor is from a point 5° C. higher than the reaction temperature to about 85° C. The amount of the vapor to be supplied can be easily calculated and prescribed on the basis of the thermal balance of the reaction zone. The feeding of the vapor into the liquid phase of the oxidation reaction system is not limited to that from one feed inlet. It is possible to secure uniform dispersion of the vapor in the liquid phase of the oxidation reaction system by feeding the vapor from a plurality of feed inlets.

The reaction in accordance with this invention may be performed continuously or batchwise by using conventional reaction vessels. Preferably, the inner wall of the reaction vessel is lined with a non-metallic material such as glass or resins in order to prevent the decomposition of hydrogen peroxide or other side-reactions. A distillation tower may be connected to the upper part of the reaction vessel so as to perform smoothly the azeotropic distillation of water and the aromatic hydrocarbon (or inert solvent).

The reaction can be carried out by intimately contacting an aqueous solution phase containing the acid catalyst and hydrogen peroxide and an oil phase containing the hydroxyalkyl-substituted aromatic hydrocarbon and the aromatic hydrocarbon solvent by mechanical stirring or by stirring effected by blowing of vapor. The azeotrope which leaves the top of the reaction vessel is condensed, and the oil phase is separated from the aqueous phase. The oil phase can be recycled to the reaction vessel. Preferably, an amount of the aqueous phase which corresponds to the amount formed by this oxidation reaction is discharged out of the reaction system, and the excess is again recycled to the reaction vessel.

On standing, the reaction mixture can be separated into the oil phase and the aqueous phase, and the aqueous phase can be recycled to the reaction vessel. As is conventionally known, the oil phase may be cleaved using an acid catalyst to obtain the desired phenols and carbonyl compounds.

The following Examples and Comparative Examples illustrate the process of this invention more specifically. In these examples, the yield of m-DHP and the ratio of cleavage were calculated in accordance with the following equations.

$$\text{Yield of m-DHP} = \frac{\text{Moles of m-DHP increased}}{\text{Moles of m-HHP and m-DC fed}} \times 100$$

$$\text{Ratio of cleavage} = \frac{\text{Moles of hydroperoxide decrease*}}{\text{Moles of hydroperoxide fed*}} \times 100$$

*Hydrogen peroxide is regarded as hydroperoxide.

EXAMPLES 1 TO 3

(1) m-Diisopropylbenzene was oxidized with air at 100° C. in the presence of an aqueous solution of sodium hydroxide. After the oxidation, toluene was added, and the separated alkaline aqueous layer was removed to afford a toluene solution of the oxidation reaction product having the composition shown in Table 1.

TABLE 1

| Components | Content (% by weight) |
| --- | --- |
| m-HHP | 10.0 |
| m-DC | 1.4 |
| m-DHP | 26.9 |
| Toluene | 48.3 |
| Water | 3.0 |
| Others | 10.4 |

(2) Into a tank-type reactor equipped with a distillation tower and a water-separating device at its upper portion and a gas blowing tube at its lower portion, the toluene solution of the oxidation product prepared as described in (1) above was introduced at a rate of 487 parts by weight/hr, and an aqueous solution containing 25% by weight of hydrogen peroxide and 12% by weight of sulfuric acid was fed at a rate of 449 parts by weight/hr. Simultaneously, a vapor of toluene heated to each of the temperatures shown in Table 2 was introduced into the reactor through the gas blowing tube at a rate of 223 parts by weight/hr. While maintaining the reaction temperature and pressure at the values shown in Table 2, the reaction was carried out with an average residence time of 10 minutes. All the toluene in the distillate from the top of the reactor was returned to the reaction system. In the meantime, 35 parts by weight/hr of the aqueous layer separated from the distillate was withdrawn out of the reaction system. The reaction mixture was continuously withdrawn from an overflowing line, and the oil phase was separated from the aqueous phase. The aqueous phase was recycled after adjusting the concentrations of the hydrogen peroxide and sulfuric acid to the aforesaid values. The total concentrations of the hydroperoxide and m-DHP in the oil and aqueous phases were measured, and the yield of m-DHP and the cleavage ratio were calculated from these values. The results are shown in Table 2.

TABLE 2

| Example | 1 | 2 | 3 |
| --- | --- | --- | --- |
| Reaction temperature (°C.) | 50 | 55 | 60 |
| Temperature of the toluene vapor (°C.) | 75 | 80 | 83 |
| Reaction pressure (mmHg) | 155 | 200 | 225 |
| Yield of m-DHP (%) | 91 | 90 | 87 |
| Ratio of cleavage (%) | 1.0 | 1.2 | 1.5 |
| Loss of hydrogen peroxide (%) | 0.25 | 0.32 | 0.36 |

COMPARATIVE EXAMPLES 1 TO 3

Into a tank-type reactor equipped with a stirrer and having a distillation tower and a water-separating device at its upper portion and a warm water jacket at its outside, the toluene solution of the oxidation reaction product prepared in Examples 1 to 3, (1) and diluted to 1.46 times with toluene was fed at a rate of 710 parts by weight/hour, and an aqueous solution containing 25% by weight of hydrogen peroxide and 12% by weight of sulfuric acid was fed at a rate of 449 parts by weight/hr. The reaction was performed with an average residence time of 10 minutes while maintaining the temperature of the warm water in the jacket, the reaction temperature, and the reaction pressure at the values shown in Table 3. The distillate from the top of the reactor and the reaction mixture withdrawn from an overflowing line were treated in the same time as in Examples 1 to 3. The results are shown in Table 3.

TABLE 3

| Comparative Example | 1 | 2 | 3(*) |
| --- | --- | --- | --- |
| Reaction temperature (°C.) | 50 | 55 | 60 |
| Temperature of the jacket (°C.) | 60 | 70 | 75 |
| Reaction pressure (mmHg) | 155 | 200 | 225 |
| Yield of m-DHP (%) | 80 | 76 | 70 |
| Ratio of cleavage (%) | 6.5 | 9.1 | 11.0 |
| Loss of hydrogen peroxide (%) | 0.27 | 0.34 | 0.39 |

(*): In 10 hours after the initiation of the reaction, the temperature of the reaction mixture rose abruptly, and thereafter, the reaction could not be continued.

COMPARATIVE EXAMPLE 4

A tank-type reactor equipped with a distillation tower and a water-separating device at its upper portion and a gas blowing tube at its lower portion was charged with the toluene solution of the oxidation reaction product prepared in Examples 1 to 3, (1) at a rate of 487 parts by weight/hr, and an aqueous solution containing 25% by weight of hydrogen peroxide and 12% by weight of sulfuric acid at a rate of 449 parts by weight/hr. Simultaneously, nitrogen gas heated to the temperature shown in Table 4 was introduced from the gas blowing tube at a rate of 3683 parts by weight/hr, and the reaction was performed with an average residence time of 10 minutes while maintaining the reaction temperature and pressure at the values shown in Table 4. All the toluene in the distillate from the top of the reactor was returned to the reaction system, and in the meantime, 35 parts by weight/hr of the aqueous phase separated from the distillate was withdrawn out of the system. The reaction mixture was withdrawn continuously from an overflowing line, and was separated into an oil phase and an aqueous phase. The aqueous phase was recycled after the concentrations of hydrogen peroxide and sulfuric acid contained in it were adjusted to the values described above. The total concentrations of hydroperoxide and m-DHP in the oil and aqueous phases were measured, and based on the measurements, the yield of m-DHP, the ratio of cleavage, and the percent loss of hydrogen peroxide entrained in the distilled aqueous phase were calculated. The results are shown in Table 4.

TABLE 4

| | |
| --- | --- |
| Reaction temperature (°C.) | 50 |
| Temperature of nitrogen gas (°C.) | 75 |
| Reaction pressure (mmHg) | 225 |
| Yield of m-DHP (%) | 87 |
| Ratio of cleavage (%) | 2.5 |
| Loss of hydrogen peroxide (%) | 7.5 |

EXAMPLE 4

(1) A toluene solution of the oxidation reaction product having the composition shown in Table 5 was prepared from p-diisopropylbenzene in the same way as in Examples 1 to 3, (1).

TABLE 5

| Components | Content (wt %) |
| --- | --- |
| p-HHP | 10.0 |
| p-DC | 1.4 |
| p-DHP | 26.9 |
| Toluene | 48.3 |
| Water | 3.0 |
| Others | 10.4 |

(2) The toluene solution obtained as described in (1) above was reacted in the same way as in Examples 1 to 3 under the conditions shown in Table 6 below. The results are also shown in Table 6.

TABLE 6

| | |
| --- | --- |
| Reaction temperature (°C.) | 50 |
| Temperature of the toluene vapor (°C.) | 75 |
| Reaction pressure (mmHg) | 155 |
| Yield of p-DHP (%) | 93 |
| Ratio of cleavage (%) | 1.2 |
| Loss of hydrogen peroxide (%) | 0.24 |

What we claim is:

1. A process for the preparation of an aromatic hydroperoxide by oxidizing a hydroxyalkyl-substituted aromatic compound having at least one hydroxyalkyl group directly bonded to an aromatic ring carbon of the aromatic compound and being represented by the formula:

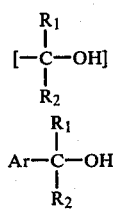

wherein Ar represents a benzene or naphthalene ring and $R_1$ and $R_2$ each represent a lower alkyl group, with hydrogen peroxide in the presence of an acid catalyst in a heterogeneous system of a water-immiscible inert aromatic hydrocarbon solvent at a reaction temperature of up to about 70° C. while removing by-product water as an azeotrope with the aromatic hydrocarbon solvent in the oxidation system; characterized in that said oxidation is carried out while feeding a vapor of a water-immiscible inert aromatic hydrocarbon solvent having a temperature higher than the reaction temperature but not exceeding about 90° C. into a liquid phase of the oxidation system.

2. The process of claim 1 wherein the hydroxyalkyl-substituted aromatic compound is an oxidation product of m-diisopropylbenzene composed of m-diisopropylbenzene dihydroperoxide and by-product m-substituted carbinol hydroperoxide and/or dicarbinol.

3. The process of claim 1 wherein the amount of the hydrogen peroxide is about 0.5 to about 20 equivalents per mole of the hydroxyl groups of the hydroxyalkyl-substituted aromatic compound.

4. The process of claim 1 wherein the concentration of the acid catalyst in an aqueous solution of hydrogen peroxide in the oxidation system is from about 0.5 to about 5 moles/liter.

5. The process of claim 1 wherein the oxidation is carried out at a pressure of from about 30 to about 300 mm Hg.

6. The process of claim 1 wherein the aromatic hydrocarbon solvent in the oxidation system is selected from the group consisting of benzene, toluene, xylene and ethylbenzene.

7. The process of claim 1 wherein the aromatic hydrocarbon solvent vapor is a vapor of a solvent selected from the group consisting of benzene, toluene, xylene and ethylbenzene.

8. The process of claim 1 wherein the temperature of the aromatic hydrocarbon solvent vapor is from a temperature 5° C. higher than the reaction temperature to about 85° C.

9. The process of claim 1 wherein Ar represents a benzene ring which may be substituted by alkyl or hydroperoxyalkyl.

10. The process of claim 1 which comprises oxidizing said hydroxyalkyl-substituted aromatic compound at a pressure of from about 30 to about 300 mm Hg with from about 0.5 to about 20 equivalents of hydrogen peroxide per mole of the hydroxyl groups of the hydroxyalkyl-substituted aromatic compound in the presence of an acid catalyst in an aqueous solution of the hydrogen peroxide at a concentration of from about 0.5 to about 5 moles/liter in a heterogeneous system of a water-immiscible inert aromatic solvent selected from the group consisting of benzene, toluene, xylene and ethylbenzene at a reaction temperature of up to about 70° C. while removing by-product water as an azeotrope with the aromatic hydrocarbon solvent in the oxidation system, said oxidation being carried out while feeding a vapor of a water-immiscible inert aromatic hydrocarbon solvent selected from the group consisting of benzene, toluene, xylene and ethylbenzene at a temperature ranging from 5° C. higher than the reaction temperature to about 85° C., into a liquid phase of the oxidation system.

11. The process of claim 10 wherein the hydroxyalkyl-substituted aromatic compound is an oxidation product of m-diisopropylbenzene composed of m-diisopropylbenzene dihydroperoxide and by-product m-substituted carbinol hydroperoxide and/or dicarbinol.

12. The process of claim 10 wherein the reaction temperature is in the range of from about 30° C. to about 60° C.

* * * * *

UNITED STATES PATENT AND TRADEMARK OFFICE
CERTIFICATE OF CORRECTION

PATENT NO. : 4,267,387
DATED : May 12, 1981
INVENTOR(S) : Imai et al.

It is certified that error appears in the above—identified patent and that said Letters Patent is hereby corrected as shown below:

On title page, please add the following Foreign Application Priority Data (item [30]):

October 17, 1978 [JP] Japan .............. 53/126851 --.

Signed and Sealed this

Eighteenth Day of August 1981

[SEAL]

Attest:

GERALD J. MOSSINGHOFF

Attesting Officer

Commissioner of Patents and Trademarks